United States Patent
Chapman et al.

(10) Patent No.: US 7,672,430 B2
(45) Date of Patent: Mar. 2, 2010

(54) AREA X-RAY OR UV CAMERA SYSTEM FOR HIGH-INTENSITY BEAMS

(75) Inventors: Henry N. Chapman, Livermore, CA (US); Sasa Bajt, Livermore, CA (US); Eberhard A. Spiller, Livermore, CA (US); Stefan Hau-Riege, Fremont, CA (US); Stefano Marchesini, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 21 days.

(21) Appl. No.: 12/121,177

(22) Filed: May 15, 2008

(65) Prior Publication Data
US 2009/0116619 A1 May 7, 2009

Related U.S. Application Data

(60) Provisional application No. 60/930,435, filed on May 15, 2007.

(51) Int. Cl.
*G01N 23/20* (2006.01)
(52) U.S. Cl. .............................. 378/71; 378/87; 378/145
(58) Field of Classification Search ............. 378/70–90, 378/145; 250/372
See application file for complete search history.

(56) References Cited

U.S. PATENT DOCUMENTS 6,809,864 B2 * 10/2004 Martynov et al. ............ 359/576
2007/0009091 A1 * 1/2007 Terada ......................... 378/70

OTHER PUBLICATIONS

Marchesini, S. et al. X-ray image reconstruction from a diffraction pattern alone, *Phys. Rev. B* 68 (114), 140101, (2003).
Montcalm, C. et al. Multilayer reflective coatings for extreme-ultraviolet lithography, $23^{rd}$ Annual International Symposium on Microlithography, Santa Clara, CA Feb. 22-27, 1998, Lawrence Livermore National Laboratory.

* cited by examiner

*Primary Examiner*—Jurie Yun
(74) *Attorney, Agent, or Firm*—John H. Lee; Michael C. Staggs (57) ABSTRACT

A system in one embodiment includes a source for directing a beam of radiation at a sample; a multilayer mirror having a face oriented at an angle of less than 90 degrees from an axis of the beam from the source, the mirror reflecting at least a portion of the radiation after the beam encounters a sample; and a pixellated detector for detecting radiation reflected by the mirror. A method in a further embodiment includes directing a beam of radiation at a sample; reflecting at least some of the radiation diffracted by the sample; not reflecting at least a majority of the radiation that is not diffracted by the sample; and detecting at least some of the reflected radiation. A method in yet another embodiment includes directing a beam of radiation at a sample; reflecting at least some of the radiation diffracted by the sample using a multilayer mirror; and detecting at least some of the reflected radiation.

27 Claims, 8 Drawing Sheets

AREA X-RAY OR UV CAMERA SYSTEM FOR HIGH-INTENSITY BEAMS

RELATED APPLICATIONS

This application claims priority to provisional U.S. application Ser. No. 60/930,435 filed on May 15, 2007, which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to camera systems, and more particularly to X-ray or Ultraviolet (UV) camera systems.

BACKGROUND

While various techniques are known in the art for analyzing materials, there remains a need for an area X-ray or UV camera system for high-intensity beams.

SUMMARY

A system in one embodiment includes a source for directing a beam of radiation at a sample; a multilayer mirror having a face oriented at an angle of less than 90 degrees from an axis of the beam from the source, the mirror reflecting at least a portion of the radiation after the beam encounters a sample; and a pixellated detector for detecting radiation reflected by the mirror.

A system in another embodiment includes a source for directing an X-ray beam at a sample; a multilayer mirror being oriented at an angle of less than 90 degrees from an axis of the X-ray beam from the source, the mirror reflecting at least a portion of the X-rays after the X-ray beam encounters a sample; and a pixellated detector for detecting X-rays reflected by the mirror.

A method in a further embodiment includes directing a beam of radiation at a sample; reflecting at least some of the radiation diffracted by the sample; not reflecting at least a majority of the radiation that is not diffracted by the sample; and detecting at least some of the reflected radiation.

A method in yet another embodiment includes directing a beam of radiation at a sample; reflecting at least some of the radiation diffracted by the sample using a multilayer mirror; and detecting at least some of the reflected radiation.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 4, section ($a$) is a diffraction pattern from one particular test object, recorded with a single pulse, using the experimental system of FIG. 3.

FIG. 4, section ($b$) is a second diffraction pattern from the test object, taken 20 s after the first exposure of FIG. 4, section ($a$).

FIG. 5, section ($a$) is a Scanning Electron Microscope (SEM) image of the test sample before exposure to a beam.

FIG. 5, section ($b$) is an image reconstructed from the diffraction pattern of FIG. 4$a$.

FIG. 5, section ($c$) is a SEM image of the test sample after exposure to a beam.

FIG. 5, section ($d$) is an image reconstructed from the diffraction pattern of FIG. 4, section ($a$).

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

A system in one general embodiment includes a source for directing a beam of radiation at a sample; a multilayer mirror having a face oriented at an angle of less than 90 degrees from an axis of the beam from the source, the mirror reflecting at least a portion of the radiation after the beam encounters a sample; and a pixellated detector for detecting radiation reflected by the mirror.

A system in another general embodiment includes a source for directing an X-ray beam at a sample; a multilayer mirror being oriented at an angle of less than 90 degrees from an axis of the X-ray beam from the source, the mirror reflecting at least a portion of the X-rays after the X-ray beam encounters a sample; and a pixellated detector for detecting X-rays reflected by the mirror.

A method in one general embodiment includes directing a beam of radiation at a sample; reflecting at least some of the radiation diffracted by the sample; not reflecting at least a majority of the radiation that is not diffracted by the sample; and detecting at least some of the reflected radiation.

A method in yet another general embodiment includes directing a beam of radiation at a sample; reflecting at least some of the radiation diffracted by the sample using a multilayer mirror; and detecting at least some of the reflected radiation.

Much of the following discussion shall be described in terms of a system using X-rays. However, it should be understood that other types of radiation, including Ultraviolet (UV) light, etc., may be used in any of the embodiments described herein unless otherwise noted. An X-ray (or Röntgen ray) is a form of electromagnetic radiation with a wavelength in the range of 10 to 0.01 nanometers (nm), corresponding to frequencies in the range 30 PHz to 30 EHz. Extreme Ultraviolet (EUV) light has a wavelength in the range of 121 nm to 10 nm. Vacuum Ultraviolet (VUV) light has a wavelength in the range of 200 nm to 10 nm.

Figure 1:
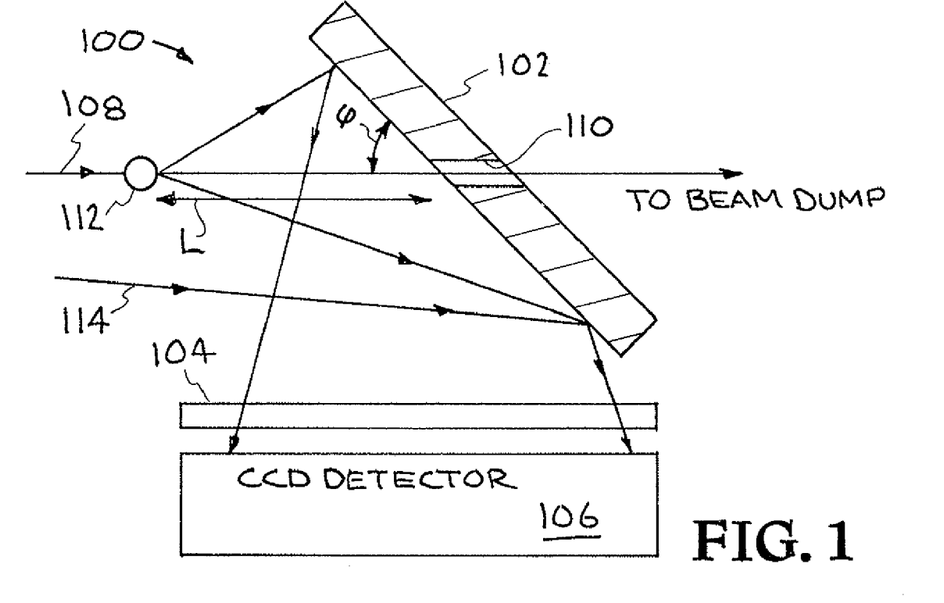
FIG. 1 is a side view of a system according to one embodiment.

FIG. 1 illustrates an area X-ray camera system 100 which includes a multilayer mirror 102, an optional filter 104 for blocking a wavelength that is not of interest, and a pixellated detector 106 such as a direct-illumination charge-coupled device (CCD).

The multilayer mirror is inclined at an angle φ to the direct radiation beam 108. The angle is preferably less than 90 degrees, e.g., between about 10 and about 80 degrees from the axis of the beam.

An aperture 110 in the mirror allows radiation from the beam that is not scattered by the sample to pass through it. The weaker scattered beam from the sample 112 under investigation is reflected from the mirror onto the pixellated detector. The parasitic ray 114, due to scattering from an object further upstream (e.g. the focusing optic), is either not reflected by the mirror or reflected away from the pixellated detector.

To achieve high resolution, the camera preferably intercepts a large solid angle of scattered light, and so the mirror preferably reflects a large range of angles. Therefore the mirror may be coated with a multilayer that was graded so that the Bragg condition is matched for all rays hitting the mirror and which originate at the sample. In a particularly preferred embodiment, the multilayer mirror has a layer period that varies across the face of the mirror in such a way that the X-ray wavelength of interest reflects at highest reflectivity only when the ray originates from the sample position. That is, the modification of Bragg's law, to take into account refraction by the multilayer materials, $$\lambda = 2d\sin\theta\sqrt{1 - \frac{2\delta}{\sin^2\theta}}$$ Equation 1 is obeyed for a particular wavelength λ by varying d according to the angle of incidence θ for rays originating at the sample and reflecting at all points across the mirror. In the equation above, δ is the average real part of the refractive index of the multilayer, and d is the spacing between the planes in the atomic lattice.

Rays originating from the sample 112 will be incident on the mirror at different angles of incidence θ. Therefore, to obey Equation 1 across the face of the mirror, the d spacing must vary across the face of the mirror in relationship with the variation in angle θ. The d spacing variation is suitable only for one wavelength λ. The d spacing varies across the face of the mirror with a radial dependence. Lines of constant d spacing are circles that are centered on the point that is the perpendicular intersection to the mirror plane from the sample point. For a distance r from that point of intersection, on the surface of the mirror, the incidence angle is given by $$\tan\theta = \frac{1}{\sqrt{2}\,r}$$ Equation 2

From Equation 1 the thickness profile is then given by $$d(r) = \frac{\lambda}{2\sqrt{l^2/(l^2 + 2r^2) - 2\delta}}$$ Equation 3

Conventional techniques may be used to control deposition profiles of the various layers of the mirror may be used. For example, known methods of using shadow masks to control deposition profiles may be used.

The mirror may comprise laminated layers of various materials. For example, the laminated layers may be made from combinations of two or more of the following materials: Si, Mo, $B_4C$, Co, Ni, C, Ru, Y, Cr, $SiO_2$, $TiO_2$. Other reflective materials/structures may be used as well.

An example of the use of a system in one embodiment is to measure scattering, diffraction, or interference patterns at a soft-X-ray free-electron laser (FEL). The FEL in one approach emits intense ultrashort pulses of soft-X-rays, which are focused onto a sample under investigation. The forward scattering is measured from the sample (e.g. to determine the dynamics of the material under irradiation by the FEL pulse itself or by another pulse synchronized to the FEL pulse). For soft X-rays and most microscopic samples, the fraction of light scattered by the object is small and the unscattered direct beam carries most of the incident energy. If this beam were to illuminate the pixellated detector, it might ablate material and damage it, It instead passes through a hole in a plane multilayer mirror, and continues to a beam dump far away from the experiment. In this example, assume the multilayer mirror is oriented at 45 degrees to the direct beam, and in this configuration the hole is oriented to be parallel to the direct beam. The pixellated detector is oriented at twice the mirror inclination angle, or 90 degrees, so as to be normal to the axis of the reflected light. The pixellated detector detects the scattered light from the sample that is reflected by the mirror.

Note that it is not necessary that the multilayer mirror be incident at 45 degrees to the beam. For shorter wavelength X-rays it is easier to make multilayer coatings that reflect at more grazing angles, e.g., less than 45 degrees, and so in this case the system may be configured with the multilayer mirror at a more grazing angle than 45 degrees, and the pixellated detector would be oriented at about twice this grazing angle. Note that the grazing angle may be limited by the angular acceptance of the detector. Also, a particular resolution for a particular wavelength may dictate a numerical aperture or half angle of acceptance of the detector. For a planar mirror, the grazing angle of the mirror (at the intersection point with the direct beam axis) is preferably as least as large as this acceptance half angle, and so the largest angle of reflection is preferably at least as large as the entire acceptance full angle.

As noted above, the multilayer mirror may have a planar face. In other embodiments the multilayer mirror can be concave or convex. For example, to increase the distance between the mirror (and pixellated detector) to the sample, for a fixed pixellated detector size, a concave mirror may be used that acts to converge the scattered rays onto the pixellated detector. Ideally, the concave mirror is an ellipsoid, with one focus at the sample position, and the other along the reflected beam path, some distance behind the pixellated detector.

In another embodiment, the multilayer mirror can include an antireflection coating for a specific wavelength. Preferably, the antireflection coating caps the mirror. The antireflective coating may be used, for example, to suppress diffraction in the first harmonic of the FEL radiation. In this case the multilayer coating is tuned for a higher harmonic wavelength, such as the third harmonic at 10.6 nm. Mirrors that reflect the second harmonic of the FEL beam and which suppress the first harmonic with an anti-reflection coating are also possible. Such embodiments can be used to study the interaction of matter with intense X-ray pulses at higher resolution than what can be achieved with the longer first harmonic wavelength, and can be used to study high-energy density plasma properties.

Advantages of various embodiments of the system include that the strong direct beam does not illuminate the detector, which could possibly damage it; a beamstop is not required in front of the detector, which could scatter and contaminate the measurement; and the multilayer mirror only reflects light of within the bandpass of the multilayer that originates from the sample position. Parasitic scattering, for example, may be filtered by the mirror.

Additional advantages of various embodiments is that the camera system may be sensitive to a particular bandpass of the multilayer mirror, so out of band emission from the sample (e.g. from the glow of the plasma that occurs long after the pulse has traversed the sample) is filtered out. The camera may also be sensitive to ray direction, so parasitic scattering (e.g. from the focusing optics upstream from the sample) is also filtered out.

Illustrative uses for embodiments of the present invention includes ultrafast imaging of microscopic images using soft-X-ray and EUV free-electron lasers. This may include ultrafast time-resolved imaging of crack propagation in a nanoparticle. Other uses include imaging diagnostics for plasmas. Further uses include imaging of biological materials at resolutions beyond the radiation damage limit, e.g., by using intense pulses from soft-X-ray FELs.

Additional uses for embodiments of the present invention include diffraction imaging of exploding particles, discussed in more detail in the U.S. Provisional Patent Application incorporated by reference; injected particles; pump-probe imaging; high-resolution imaging of diatoms (at shorter wavelength), etc.

Further embodiments may employ shorter wavelengths for higher resolution and uniform heating. For example, mirrors for wavelengths of 3 nm and shorter are contemplated. A higher pulse energy may be used for single-particle single-shot imaging. A high-repetition shutter may be employed.

Figure 2:
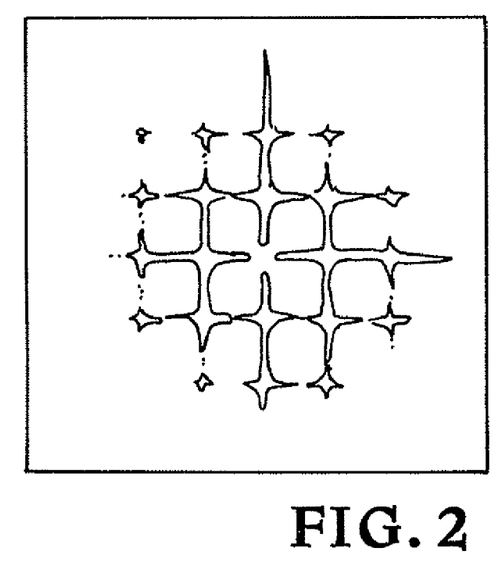
FIG. 2 is a diffraction pattern measured at a wavelength of 32 nm using one embodiment.

Several embodiments of the camera with a 45 degree planar mirror were put into practice in experiments carried out at an EUV-FEL. The mirrors for these cameras were manufactured at Lawrence Livermore National Laboratory for wavelengths of 32 nm, 16 nm, 13.5 nm, 10 nm, 6.9 nm, and 4.5 nm, all for a sample to mirror distance L (FIG. 1) of 35 mm. The mirror and camera accepted a range of scattering angles from −15 degrees to +15 degrees. An example of a diffraction pattern recorded is shown in FIG. 2. We show a pattern from an object consisting of a grid of microfabricated holes, which was used to determine the uniformity of the camera's efficiency. It is found that the efficiency, and hence the mirror reflectivity was uniform to less than 5% variation. The pattern shown in the figure also demonstrates an advantage of using a hole in the mirror instead of a beamstop for the direct beam. In experiments at synchrotrons it is found that the beamstop scatters radiation that contaminates the measurement near the center of the pattern. If the reflectivity of the mirror near the hole had a sharp cutoff to zero in the hole, then this transition would cause diffraction with similar properties to a sharp-edged beamstop. This may be acceptable for some uses. However, in a preferred approach, the reflectivity falls gently to zero over about a 1 mm (e.g., 1 mm±0.4 mm) distance from the aperture edge towards the center of the aperture. This may be effected by, or be a natural phenomenon of, making the mirror substrate rougher near where the aperture was drilled. The roughness reduces the reflectivity of the mirror near the edge of the aperture.

Theoretical studies and simulations predict that with a very short and very intense coherent X-ray pulse a single diffraction pattern may be recorded from a large macromolecule, a virus, or a cell without the need for crystalline periodicity. Measurement of the over-sampled X-ray diffraction pattern permits phase retrieval and hence structure determination. Although individual samples may be destroyed by the X-ray pulse, a three-dimensional data set may be assembled when copies of a reproducible sample are exposed to the beam one by one, The challenges in carrying out such an experiment are significant, and engage an interdisciplinary approach drawing upon structural biology, atomic and plasma physics, mathematics, statistics, and X-ray laser physics.

The following description includes experimental verification of the principle of flash diffraction imaging using the first soft X-ray free-electron laser, the VUV-FEL. The results show that an interpretable diffraction pattern can be obtained before the sample turns into a plasma when exposed to an intense 25 femtosecond (fs) long photon pulse at 32 nm wavelength (focused to a peak intensity of up to $10^{14} W/cm^2$). Significantly, the image obtained by phase retrieval and inversion of the diffraction pattern shows no discernible sign of damage, and the object was reconstructed to the resolution limit. Damage occurs only after the pulse traverses the sample. A second exposure shows scattering from the hole that was created by the first pulse. These results provide experimental evidence for the basic principle of flash imaging, and have implication for studying non-periodic molecular structures in biology and in any other area of science and technology where structural information with very high spatial and temporal resolution is valuable.

The first free-electron laser (FEL) to reach the soft-X-ray regime is the Vacuum Ultra-Violet Free-Electron Laser (VUV-FEL) located at the Deutsches Elektronen-Synchrotron (DESY) in Hamburg, Germany. This facility has opened up new fields of investigation utilizing intense, ultrashort pulses of short-wavelength radiation to probe matter at fine length and time scales. The generation of X-ray pulses is based on the principle of self-amplification of spontaneous emission (SASE), and for the experiment described here the VUV-FEL was operated in a single bunch ultrashort pulse mode resulting in coherent FEL pulses that were close to transform limited. The FEL pulse was typically dominated by a single mode, i.e., it had almost complete transverse and longitudinal coherence. The mean photon wavelength was 32 nm, the average pulse energy was about 8 μJ, equivalent to about $10^{12}$ photons, and the pulse duration was 25±5 fs. A metric to characterize how much light is available for experiments that require coherence, such as holography or coherent imaging, is the peak spectral brilliance. For the VUV-FEL the spectral brilliance of a single pulse is up to $10^{28}$ photons/(s $mm^2$ $mrad^2$ 0.1% bandwidth), which is seven orders of magnitude higher than the peak brilliance of the most advanced synchrotron radiation sources. This high degree of coherence is a requirement for high-resolution imaging, using the present method, and results in the ability to utilize essentially the entire output of the source for these experiments. Hard X-ray FELs, such as the Linac Coherent Light Source, under construction at Stanford, the European X-Ray Free-Electron Laser at DESY, and the SPring-8 Compact SASE Source in Japan, will create hard X-ray pulses, which when focused on the sample, will produce five orders of magnitude higher photon intensities than the current VUV-FEL of DESY. These hard X-ray FELs will enable experiments similar to those demonstrated here to scale to much smaller objects, and will ultimately allow nanometer- to atomic-resolution imaging of nonperiodic objects. Accordingly, such hard X-ray FELs may be used in accordance with the embodiments presented herein.

Diffraction imaging is elegant in its experimental simplicity: a coherent X-ray beam illuminates the sample and the far-field diffraction pattern of the object is recorded on an area detector (in this case a direct-illuminated CCD chip). The measured diffraction intensities are proportional to the modulus squared of the Fourier transform of the wave exiting the object. On their own, these diffraction intensities are insufficient to back-transform to form an image in real space. That inversion requires knowledge of both the diffraction intensity and phase. If the diffraction pattern intensities are sampled finely enough, then it is possible to solve for the diffraction pattern phases. The solution to this non-linear inverse problem is usually obtained iteratively by sequentially enforcing known constraints in reciprocal space and in real space. Specifically, in real space we assert that the image has zero scattering strength outside the area of the object's boundary (called its support), whilst in reciprocal space the squared modulus of the Fourier transform of the image equals the measured diffraction intensities. Such algorithms have now been used successfully for image reconstruction in X-ray diffraction experiments. The algorithms usually require that the support of the object be known a priori, and the closer the support to the actual object boundary, the better the reconstruction. In this work, a support-finding algorithm called "shrinkwrap" was used, which successively refines an estimate of the support from the current estimate of the image. This algorithm does not require the support to be known and is remarkably robust at finding the smallest image support that contains the majority of the image intensity, as described in more detail below.

In principle, the real-space image obtained using phase retrieval will be equivalent to that formed by a perfect lens under the same illumination conditions and its resolution is limited by the largest scattering angle accepted by the detector. The image pixel width (half period of the finest spatial frequency recorded) is given by $\delta=\lambda/(2NA)$, where NA is the numerical aperture of the detector: the sine of the half angle subtended by the detector from the object. For our geometry of 0.26 NA and 32 nm wavelength, $\delta=62$ nm.

Figure 3:
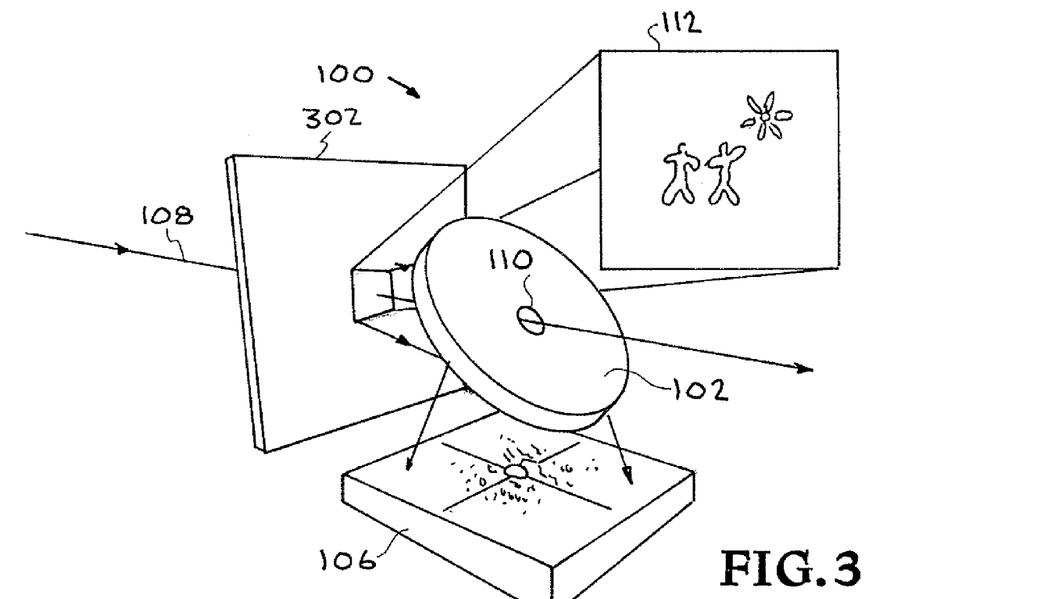
FIG. 3 is a perspective view representation of an experimental system according to one embodiment.

FIG. 3, having common parts numbered generally as in FIG. 1, is a graphical representation of the experimental geometry tailored to the VUV-FEL. As shown, the system 100 includes a graded multilayer-coated planar mirror 102 to direct the diffraction pattern onto a CCD detector 106. The mirror has an aperture 110, or hole, in the centre for the direct beam 108 to pass through. This avoids placing any material in the direct beam that would ablate after exposure, or turn into a plasma, other than the sample 112 itself. Significantly, no optical elements are placed into the direct beam that may introduce aberrations and become damaged by the intense pulse. The experiments are performed in vacuo and everything in the direct beam contributes to the diffraction pattern. The FEL beam is incident from the left and is focused to a 20-µm spot on the sample, which is a 20-nm thick transmissive silicon nitride membrane with a picture etched into it (this is enlarged in the inset). The direct beam passes through the sample window and exits the camera through a hole in the multilayer mirror. The diffracted light from the sample reflects from that mirror onto a CCD detector. Contour lines on the mirror depict lines of constant incidence angle, and correspond to constant multilayer periods on the mirror surface.

The test samples for these experiments consisted of 20-nm thick silicon nitride membranes in which 3-µm wide patterns (FIG. 3, inset) were milled using a focused-ion beam. The membrane with the pattern was held in a square silicon window 302 that is 20 µm wide.

Figure 4A:
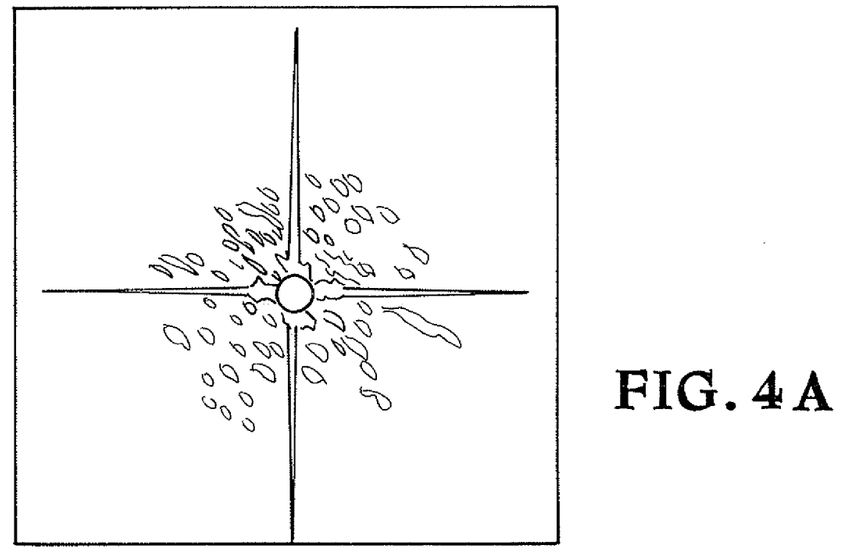
Figure 4B:
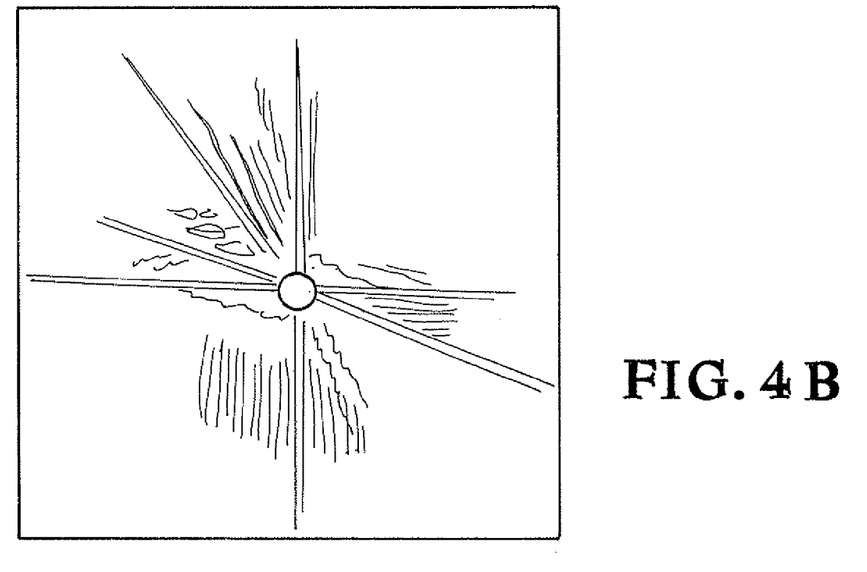

The diffraction pattern from one particular test object, recorded with a single 25±5 fs pulse, is shown in FIG. 4, section (a). The FEL pulse energy for this image was 8±2 µJ, and the peak intensity on the sample was $(4\pm2)\times10^{13}$ W/cm$^2$. The intensity is shown in FIG. 4, sections (a) and (b) on a logarithmic grey scale with black denoting 10 photons/pixel and white denoting 2000 photons/pixel for section (a) and 50,000 photons/pixel for section (b). The diffraction pattern in FIG. 4, section (a) shows the entire pattern as detected by the 0.26 NA CCD. We estimate that the absorbed energy density is approximately 20 eV/atom in the silicon nitride and that the material reached a temperature of about $6\times10^4$K before vaporizing. A second diffraction pattern taken 20 s after the first exposure for a subsequent pulse of similar intensity and duration is shown in FIG. 4, section (b). This shows diffraction from a hole left in the membrane caused by the first pulse. That is, the first pulse utterly destroyed the sample but not before a diffraction pattern of the apparently undamaged object could be recorded.

Images of the object obtained with a scanning electron microscope (SEM), before and after FEL exposure, are shown in FIG. 5. Particularly, FIG. 5, section (a) is a scanning electron microscope (SEM) image of the test sample before exposure to the FEL beam. FIG. 5, sections (b) and (d) show the image reconstructed, from the ultrafast coherent diffraction pattern of FIG. 4, section (a), by phase retrieval and inversion using the shrinkwrap algorithm. The squared modulus of the retrieved complex image is displayed on a linear grey scale from zero scattered photons/pixel (white) to $1.5\times10^6$ scattered photons/pixel (black). Pixel size in the reconstruction =62 nm in section (b), corresponding to the half period of the finest spatial frequency that can be recorded on our camera at 32 nm wavelength. This also happens to be the resolution of the reconstruction. The retrieved image clearly shows the silicon window edge (in section (d)), the FIB pattern, and dirt particles. FIG. 5, section (c) is an SEM image of the test sample after the exposures to the FEL beam, showing the square 20-µm window and some remaining silicon nitride, as well as visible damage to the silicon support caused by the non-circular beam. The scale bar for FIG. 5, sections (a) and (b) is 1 µm and the scale bar for FIG. 5, sections (c) and (d) is 5 µm.

The main features of the diffraction pattern of FIG. 4, section (a) are the speckles and the strong vertical and horizontal lines that pass through the center of the pattern. These horizontal and vertical lines are caused by diffraction from the edges of the square window frame that holds the silicon nitride membrane. Fine interference fringes can be observed along their length caused by the interference of scattering from the opposite edges of the window frame. This indicates that the real-space field of view is somewhat larger than the entire 20 µm wide window, and agrees with our known diffraction geometry: the image is 1300 pixels wide with a real-space pixel width of $\delta=62$ nm giving a real-space field width of 81 µm.

The speckles in FIG. 4, section (a) correspond to two length scales of the sample. The modulations of ~60 pixels (measured diagonally) in the diffraction pattern near the centre correspond to the narrow 2.5-µm diagonal dimension of the picture of the two people and the sun; and the finer speckles of about 16 pixels correspond to the distance between the picture object and the window frame in which it is centered. The speckles remain well defined out to the edge of the detector, although their visibility diminishes with scattering angle. This may be due to the fact that at the high diffraction angles at the edge of the NA=0.26 CCD detector, the optical path difference between rays diffracting from points in the object transversely separated by 20 μm is 0.26×20 μm=5 μm. This is comparable to the length of a 25 fs pulse, which is 7.5 μm. That is, the overlap of the beams in time (and hence interference between them) only occurs for one third of the pulse. Similar measurements could be used as diagnostics to estimate the FEL pulse coherence time.

Figure 5A:
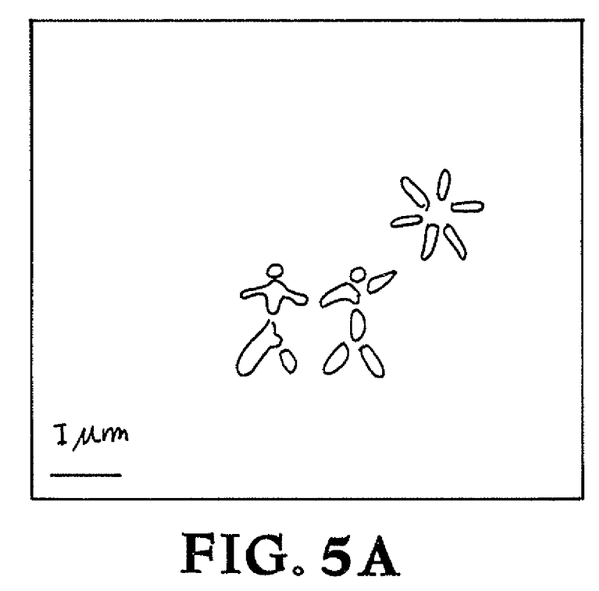
Figure 5B:
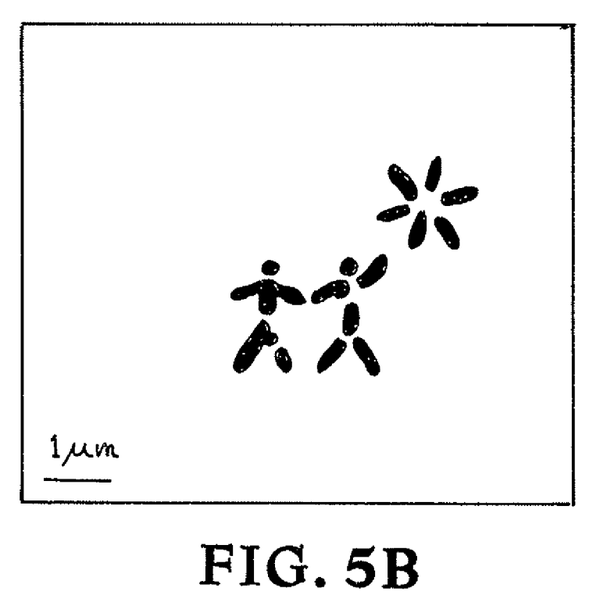
Figure 5C:
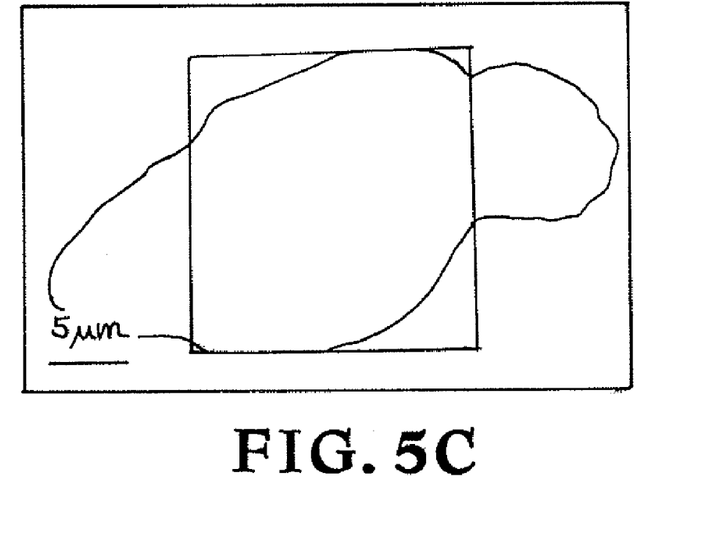
Figure 5D:
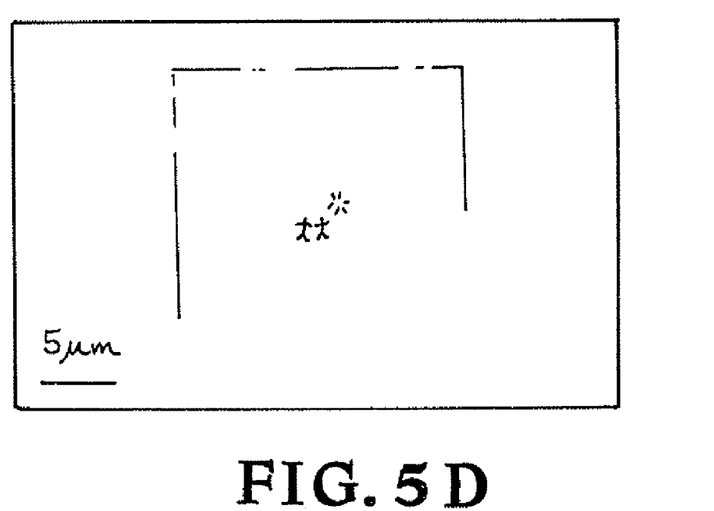
Figure 6:
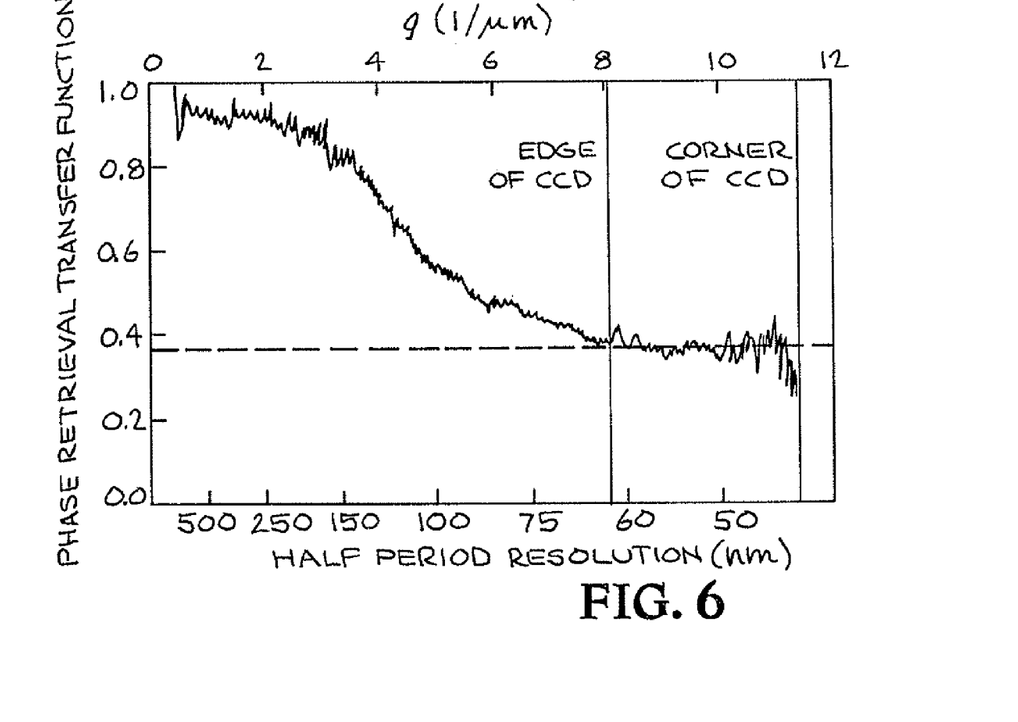
FIG. 6 is the phase-retrieval transfer function (PRTF) for the reconstructed image shown in FIG. 5, sections ($b$) and ($d$), averaged over shells of constant momentum transfer $q=(4\pi/\lambda)\sin(\theta/2)$ where $\lambda$ is the wavelength and $\theta$ the scattering angle.
Figure 7A:
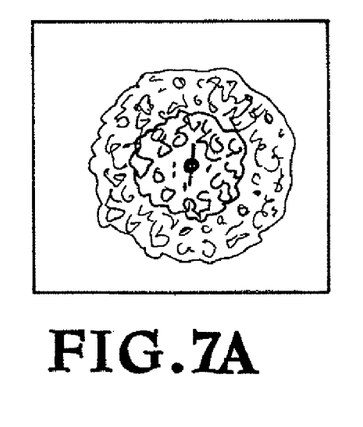
FIG. 7 depicts progression of an image reconstruction according to one approach.
Figure 7B:
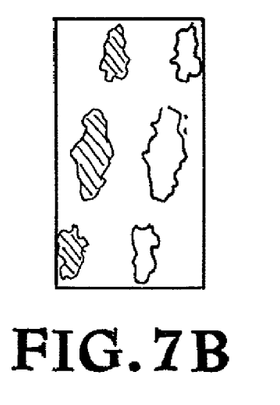
Figure 7C:
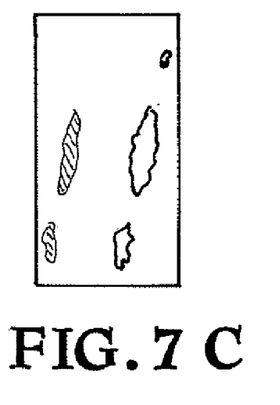
Figure 7D:
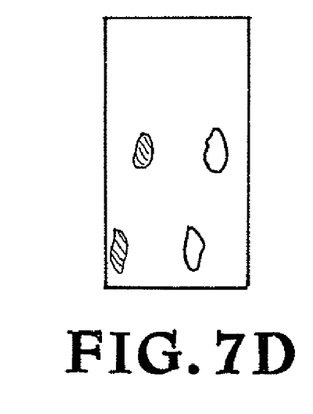
Figure 7E:
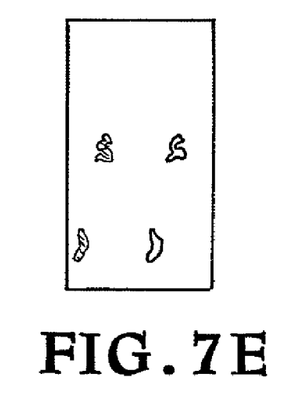
Figure 7F:
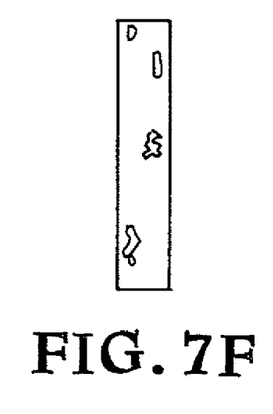

As mentioned above, FIG. 5, section (*b*) shows a real-space image of the object reconstructed from the first single shot diffraction pattern (FIG. 4, section (*a*)), obtained using the "shrinkwrap" algorithm, set forth below. The image resolution can be estimated by computing the phase-retrieval transfer function (PRTF), shown in FIG. 6. Particularly, FIG. 6 shows the PRTF for the reconstructed image shown in FIG. 5, sections (*b*) and (*d*), averaged over shells of constant momentum transfer $q=(4\pi/\lambda)\sin(\theta/2)$ where $\lambda$ is the wavelength and $\theta$ the scattering angle. This function is calculated by comparing the Fourier amplitudes of the average of multiple independent reconstructions to the measured diffraction amplitudes, and represents the confidence for which the diffraction phases have been retrieved (see text). The PRTF is equal to unity when the phase is consistently retrieved and zero when the phase is unknown. Using the convention that the resolution is given by the point where the PRTF drops to 1/e, the resolution of our reconstruction is estimated to be 62 nm.

The function of FIG. 6 represents the confidence for which the diffraction phases have been retrieved and is calculated by comparing the Fourier amplitudes of the average image of multiple independent reconstructions to the measured diffraction amplitudes normalized to the input diffraction intensities. Where the phase of a particular Fourier component is consistently retrieved, the complex values add in phase, whereas if the phase is random the sum will approach zero. The PRTF is thus equal to unity when the phase is consistently retrieved and zero when the phase is unknown. We use the convention that the resolution is given by the point where the PRTF drops to 1/e (ref. 24), which for this image occurs at the resolution limit (62 nm) set by the numerical aperture of the detector (NA=0.26) and the wavelength of the VUV-FEL pulse (32 nm).

The results shown here demonstrate the feasibility of single-shot imaging with extremely intense and ultra short soft X-ray pulses. It has also been shown that it is indeed possible to record interpretable diffraction intensities from a single FEL pulse before the sample turns into a plasma, and that the diffraction pattern carries structural information about the object before the object is destroyed. Since the method does not require any image-forming optic it can be extended to regimes for which no lens currently exists, including atomic-resolution when short-wavelength XFELs become available within the next few years.

Experimental Details

More information regarding the experiments described above with respect to FIGS. 3-6 is now presented.

Samples consisted of a 20-nm thick silicon nitride membrane suspended in a 20 μm wide square silicon window. The pattern was prepared with a dual-beam focused ion beam instrument from FEI located in the National Center for Electron Microscopy, Lawrence Berkeley National Laboratory. The pattern was milled all the way through the silicon nitride window using a 500 pA beam of 30 keV Ga+ ions. The 20 nm thick silicon nitride membrane has a transmission of 44% at a wavelength of 32 nm, and causes an estimated phase advance of 20° relative to propagation through the same length of vacuum, calculated from the known low-fluence optical constants. The samples were placed in a vacuum vessel 70 m away from the FEL undulator. The FEL pulse was focused to a 30 μm×20 μm focal spot on the sample with a 2-m focal length ellipsoidal mirror in the beam line. Single pulses are selected with a fast shutter. Due to the source coherence no aperture was needed to select a coherent patch of the beam, and no monochromator was needed to select a narrow wavelength band of the radiation.

The detector of the soft X-ray camera was a Princeton Instruments in-vacuum PI-MTE CCD camera with a back-illuminated chip of 1300×1340 square pixels of 20 μm width. The on-axis path length from the sample to the CCD was 50 mm. For 32 nm radiation and objects smaller than 20 μm, this distance is in the far field, where the diffraction pattern is equal to the Fourier transform of the exit wave . The 26-mm wide detector provides a numerical aperture of 0.26, which at 32 nm wavelength, allows a resolution of 62 nm, equal to the smallest half-period that can be imaged in the directions of the CCD rows and columns (or 43 nm in the direction of the CCD diagonal).

A multilayer mirror was used to separate the diffracted beam from the direct beam, with the direct beam passing through an aperture in the centre of the mirror. The diffracted light reflected from the resonant multilayer coating on the plane mirror and was projected onto the CCD. The superpolished flat mirror substrate was fabricated by Research Electro-Optics, Inc. The multilayer coating includes alternating layers of Si, Mo, and $B_4C$, with a period that varies across the face of the mirror from 18 nm to 32 nm. The variation in multilayer period matches the variation in the angle of incidence of rays emanating from the sample and which strike the mirror. This angle varies from 30° to 60°, as depicted by the contour lines on the mirror in FIG. 3, and the Bragg condition for 32 nm light must be maintained by varying the period by almost a factor of two over the 28-mm wide aperture of the mirror. This was achieved by sputter-depositing the multilayer materials through a rotating mask that time-averaged the deposition to give the desired material thickness at each point on the mirror. The 32-nm reflectivity across the mirror is 45%, as measured at a synchrotron-based reflectometer. The mirror serves the additional function of a bandpass filter with a bandwidth of 9 nm at the 45° angle, and so most of the broadband emission from the sample (e.g. when it turns into a plasma) is rejected by the mirror. The mirror also filters for ray direction, so that off-axis stray light will only reflect with about 1% reflectivity. Reflectivity diminishes smoothly to zero at the edge of the central hole, due to roughness of the substrate at the edge, This "soft edge" reduces scatter from the hole, whose image can be seen as a dark circle at the center of each pattern in FIG. 5.

Image reconstruction was achieved using the shrinkwrap algorithm. The iterative algorithm in one approach uses the RAAR method, which carries out projections onto the two constraint sets in a high-dimensional phase space. The dimensionality is equal to the number of phases to be retrieved; 1.7 million in this case. The constraint sets are the set of all images that have diffraction intensities equal to the measured diffraction intensities, and the set of all images that fit within the image support. The shrinkwrap algorithm updates the support constraint every 70 iterations based on the current image estimate. The shrinkwrap threshold was 0.2 times the maximum image intensity, and convolution of the magnitude of the current image estimate with a Gaussian of 3 pixels FWHM width was used, reducing to 0.7 pixels FWHM by iteration 5000. The final support is that found four update cycles prior to the point where the normalized image error exceeds a value of 0.2. This stopping criterion is typically reached in 3000 to 4000 iterations. We do not constrain the intensity or phase in the region in the mirror hole, which contains the zero spatial frequency. Also, we do not constrain the object to be real or positive. The autocorrelation of the image, formed by Fourier transformation of the diffraction intensity, clearly showed a box measuring 40 μm wide. This is the autocorrelation of the 20 μm wide window frame. During the reconstruction we set an immutable support mask containing the edges of the window formed by the intersection of two boxes of 19.5 μm and 20.5 μm wide. This immutable mask was added to a shrinking mask that was updated by the algorithm. We performed many reconstructions, starting each time from random phases. Each reconstructed image varied slightly due to the fact that with photon shot noise there is no true solution that exactly satisfies all constraint sets. However, each image determined from the final iterate was clearly recognizable as compared with the SEM image. Our image estimate, displayed in FIGS. 5b and 5d is the average of 250 independent reconstructions.

Shrinkwrap Algorithm

The aforementioned shrinkwrap algorithm is described generally below. Note that this is but one of many approaches that can be used for image reconstruction.

Ultrahigh resolution imaging may be performed without the need for a lens. The object support function is determined together with the object itself, without additional spatial information. The procedure builds on the hybrid input-output (HIO) algorithm known in the art, in which constraints are iteratively applied in real and reciprocal space, and a feedback parameter is used in real space to damp the application of the support constraint. Feedback allows this algorithm to emerge from local minima of the invariant error metric and thus avoid stagnation.

Our innovation is the simple but powerful use of the current estimate of the object to determine the support constraint. The first estimate of the support is the support of the autocorrelation function. Although this estimate is far from accurate, it is continually updated by thresholding the intensity of a blurred version of the current estimate of the object under reconstruction. Thresholding traces the boundary of the object at a given intensity contour. The blurring acts to smooth out noise, and provides a form of regularization. In turn, through the normal behavior of the HIO algorithm, the improved support constraint gives rise to yet a better estimate of the object. We find that this method is very stable, and converges to the correct support and object for both simulated and experimental x-ray diffraction data. The algorithm also successfully reconstructs complex objects (those that cause large variations in the phase of the exit wavefield in two dimensions), which hitherto have been experimentally difficult to reconstruct. This opens up the possibility of image reconstruction from microdiffraction patterns, where the illumination is tightly focused on the object.

Details of the algorithm are as follows. We start from the autocorrelation function of the object. This realspace map, obtained by Fourier transforming the diffraction pattern, displays all "interatomic" vectors, with peaks for all vectors between isolated objects, shifted to a common origin. It contains many more peaks than the object, and, even for an acentric object, possesses a center of inversion symmetry. Since the object must fit within the autocorrelation function, our first estimate of the support is a mask obtained from this function using a contour at the 4% intensity level. Both the correct object density and its centro-symmetric inversion fit within this initially centric mask, however inversion symmetry is progressively lost as the algorithm converges.

We then apply the HIO algorithm with feedback parameter $\beta=0.9$ and the real space support given by the calculated mask. We obtain the part of the diffraction pattern covered by a central beamstop from the transform of the current estimate of the object. Low frequency components are treated as free parameters. Every 20 iterations we convolve the reconstructed image (the absolute value of the reconstructed wavefield) with a Gaussian of width $\sigma$ (FWHM=2.3548$\sigma$) to find the new support mask. The mask is then obtained by applying a threshold at 20% of its maximum. The width $\sigma$ is set to 3 pixels in the first iteration, and reduced by 1% every 20 iterations down to a minimum of 1.5 pixels. Similarities of the original Gerchberg-Saxton algorithm with the "solvent flattening" method suggest that this method could be extended to crystallography.

We have tested the method using two-dimensional experimental data as well as two- and three-dimensional sets of simulated data. The experimental soft X-ray transmission diffraction pattern from two clusters of gold balls of 50±5 nm diameter deposited on a silicon nitride window was recorded at the Advanced Light Source at the Lawrence Berkeley Laboratory, using soft x-rays with a wavelength of 2.1 nm.

In FIG. 7, we present the experimental diffraction pattern and the sequence of images produced by the algorithm as it converges. Particularly, FIG. 7 shows image reconstruction from an experimental X-ray diffraction pattern. (a) X-ray diffraction pattern of a sample of 50 nm colloidal gold particles, recorded at a wavelength of 2 nm. Sections (b) to (e) shows a sequence of images produced by the algorithm as it converges. Number of iterations: 1 (b), 20 (c), 100 (d), 1000 (e). The reconstruction progresses From the autocorrelation function in (b) to an image in (e) with a steady improvement of the support boundary (shown at bottom of each frame). For comparison a SEM micrograph of the object is shown in (f). The scale bar length is 300 nm and the resolution of our reconstructed image is about 20 nm.

As shown in the first step, the algorithm starts with a support mask with perfect inversion symmetry. After a few iterations the symmetry is broken. First, one of the three regions of the mask disappears, and then the support envelope shrinks progressively around the gold ball objects. Finally, a stable solution showing excellent agreement with a scanning electron microscope image of the same object is obtained. Note that we would not expect a perfect match between the electron and x-ray images, since image formation processes are different for electrons and x-rays. Repeated computational trials have all shown the same degree of convergence to the correct image or its centro-symmetric inversion. Although after a few hundred iterations the algorithm always converged to the correct image (independent of the initial random choice of phases), as iterations were carried further both the support and the image show arbitrary displacements due to the translational invariance of the solution.

To further assess the validity of the algorithm we have tested it on several sets of simulated diffraction patterns from gold spheres and gray-scale images. The simulations all include noise and the loss of data due to a central beam-stop. They show that the algorithm is successful to the same degree as the standard HIO algorithm with tight support. As examples, we include in FIG. 8 the reconstructions of: (top row) a grayscale image; (center row) a 3D cluster of gold balls (ball diameter of 50±5 nm); and (bottom row) a complex object illuminated by a focused beam. The greyscale image demonstrates that the algorithm does not require any "atomicity" constraint provided by the gold balls. The particular 3D cluster was chosen to have a small number of balls for visualization purposes—the algorithm also works with a much larger number of balls. The third example is of particular interest since it is well known that the reconstruction of complex objects is much more difficult than real objects, but is possible using either disjoint, precisely known or specially shaped supports.

Figure 8A:
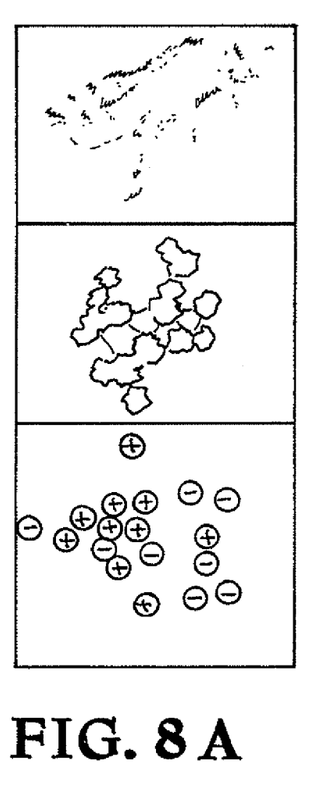
FIG. 8 depicts image reconstruction from simulated diffraction patters of a gray-scale image, a 3-D cluster of gold balls, and a complex object illuminated with a complex focused probe according to one approach.
Figure 8B:
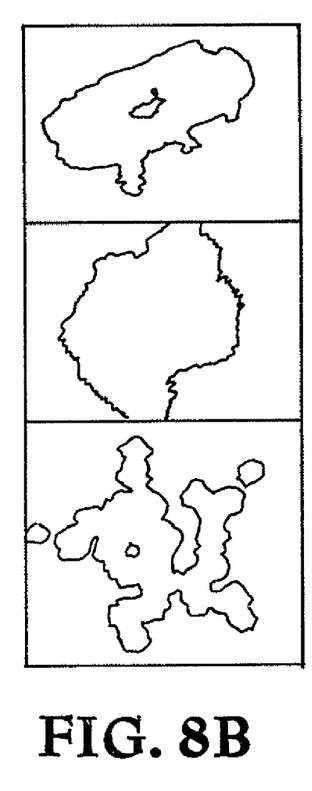
Figure 8C:
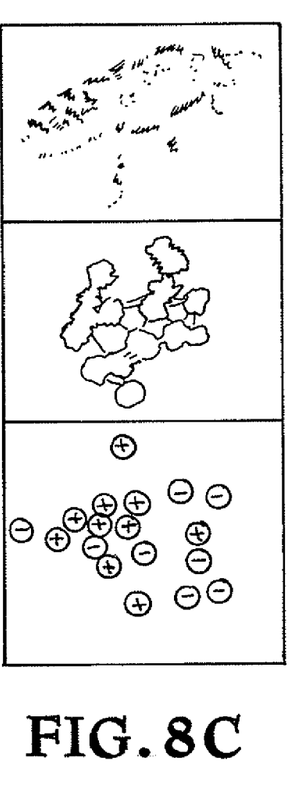

Complex objects arise in optics and X-ray diffraction in two-dimensions when large phase-shifts occur within the eikonal approximation, or if that approximation fails, in the presence of spatially dependant absorption effects, and in the presence of multiple scattering. The question arises as to whether our new method provides a sufficiently tight support, especially for objects fragmented into separated parts, to allow the inversion of complex objects. FIG. 8 (bottom) shows the reconstruction of a cluster of gold balls where each ball is multiplied by a constant random phase shift between 0 and $2\pi$. The cluster is singled-out from neighboring ones by a focused beam. A perfect match between object and reconstruction is again observed if one takes into account the translation and constant phase invariance in the solution. The result is significant because it relaxes the requirement for plane-wave illumination. The generality of the technique is thus increased because now the focused probe can be used to isolate objects in the image field.

We have compared the behavior of our algorithm to that of the HIO algorithm. The HIO algorithm requires the support a priori, and as is well known the error in the reconstruction decreases as the support becomes tighter and closer to the actual boundary of the object. This is illustrated in FIG. 9, which shows plots of the reconstruction error, as a function of Poisson noise in the diffraction intensities, for the HIO algorithm with support masks of various degrees of accuracy.

Figure 9:
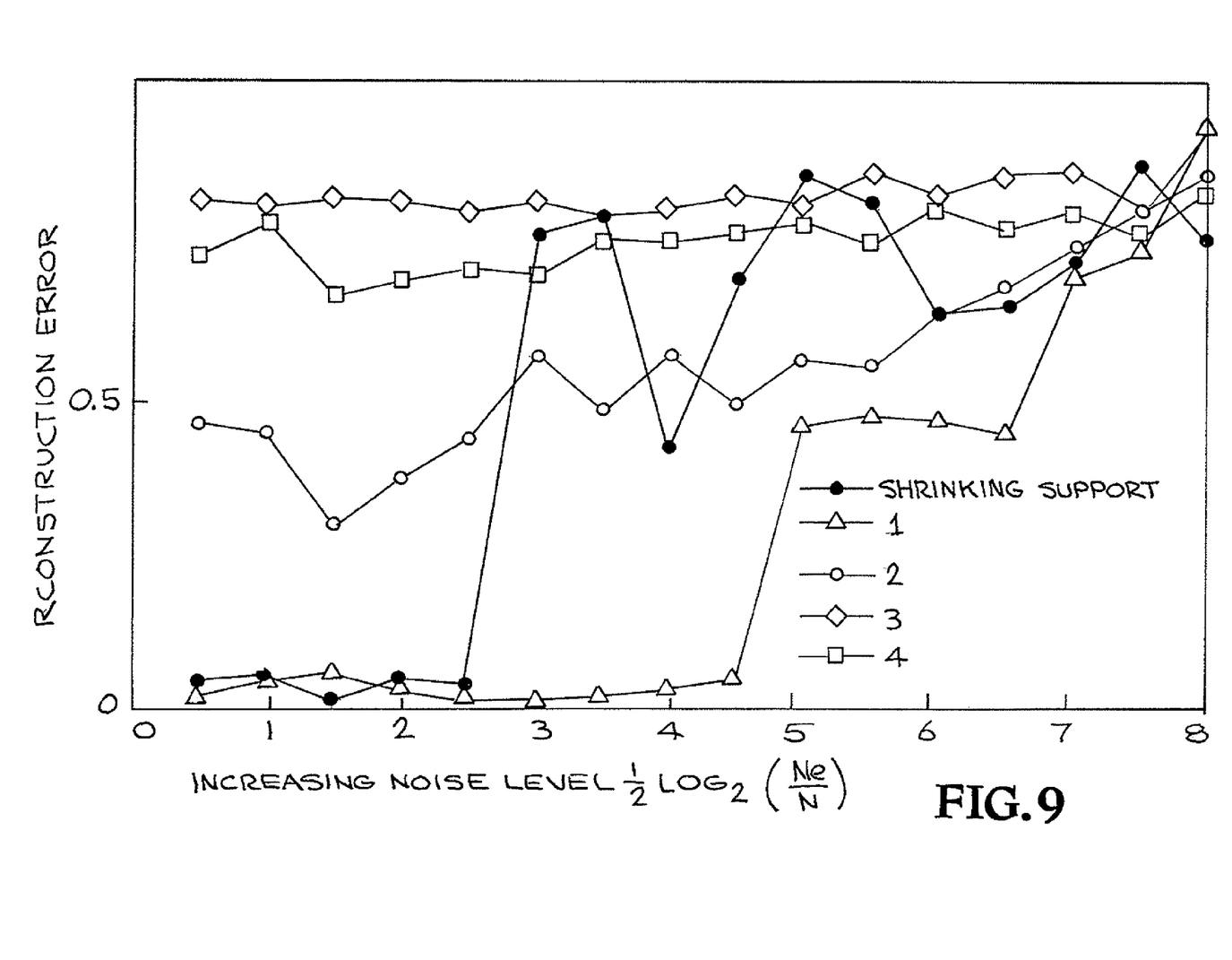
FIG. 9 is a chart showing reconstruction error as a function of Poisson noise in a diffraction image.

Particularly, FIG. 9 shows the reconstruction error of the new algorithm and the HIO algorithm for a complex object as a function of Poisson noise in the diffraction image (N is the maximum number of photons per pixel, $N_0=217$). In the HIO algorithm increasingly looser supports (support 1-4) are used: support 1, 2 and 3 are obtained by thresholding the original image after convolving with a Gaussian of 0.5, 5 and 25 pixels width. Support 4 is obtained from the autocorrelation. The HIO algorithm with perfect support (support 1) works well even for high noise levels whereas it always fails with loose supports (supports 3,4). The new algorithm (shrinking support) is superior to the HIO with limited knowledge of the support shape (support 3,4). Our algorithm fails when the noise in real space becomes larger than the threshold used to update the support.

The masks for these cases were calculated by convolving the object by Gaussians of various widths (0.5, 5, and 25 pixels) and thresholding at 5% level from the maximum. This corresponds to knowing the shape of the object to a given resolution. It is seen that even for low noise, HIO can achieve a reasonable reconstruction only if the support mask is set to the boundary known at essentially the same resolution to which we are reconstructing the object. The reconstruction error for our algorithm (which does not require a priori knowledge of the support) is also plotted in FIG. 9. We expect that the noise level at which our algorithm fails to reconstruct occurs when the noise in real space becomes larger than the threshold used to update the support. At this noise level the estimate of the support will be influenced by the noise, and the algorithm will be unable to converge to the correct boundary. This suggests that the optimum threshold setting depends on the noise level in the data, and we will only be able to reconstruct those parts of the object where the contrast is above the noise. As the support used in the HIO algorithm becomes looser, we observe our algorithm to be much superior, even in the presence of noise. This is because our algorithm always improves upon the support and so makes optimal use of the available information. The only prior knowledge needed is that the object possesses compact support (i.e. is isolated), so that oversampling diffraction conditions can be guaranteed experimentally, and that the contrast of the object is above the noise. By comparison with earlier methods, no knowledge of the shape of the object is required. There are few adjustable parameters in our algorithm; namely, support resolution, support threshold, and feedback parameter. Additional constraints can be added to strengthen convergence, such as atomicity, positivity and histogram matching.

The combination of an apparatus to measure large angle diffraction patterns with our new method of data analysis forms a new type of diffraction-limited, aberration-free tomographic microscopy. The absence of inefficient optical elements makes more efficient use of damaging radiation, while the reconstruction from a three-dimensional diffraction data set will avoid the current depth-of-field limitation of zoneplate based tomography.

The use of focused illumination will allow users to select either one or two-part objects (which may be complex) from a field. The conditions of beam energy and monochromatization used in these preliminary experiments are far from optimum for diffractive imaging and can be greatly improved to reduce recording times by more than two orders of magnitude. We expect this new microscopy to find many applications. Since dose scales inversely as the fourth power of resolution, existing measurements of damage against resolution can be used to show that statistically significant images of single cells should be obtainable by this method at 10 nm resolution in the 0.5-10 μm thickness range under cryomicroscopy conditions. Imaging by harder coherent X-rays of inorganic nanostructures (such as mesoporous materials, aerosols and catalysts) at perhaps 2 nm resolution can be expected. Atomic-resolution diffractive imaging by coherent electron nanodiffraction may be used.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
    a source for directing a beam of radiation at a sample;
    a multilayer mirror having a face oriented at an angle of less than 90 degrees from an axis of the beam from the source, the mirror reflecting at least a portion of the radiation diffracted by the sample after the beam encounters the sample; and
    a pixellated detector for detecting radiation reflected by the mirror.

2. The system of claim 1, wherein the radiation includes X-rays.

3. The system of claim 1, wherein the radiation includes ultraviolet light.

4. The system of claim 1. wherein the source is a free-electron laser.

5. The system of claim 1, wherein the mirror has an aperture therein for allowing radiation from the beam that is not scattered by the sample to pass therethrough.

6. The system of claim 5, wherein an edge of the aperture in the face of the mirror is shaped such that a reflectivity of the mirror gradually drops to zero over about a 1 mm distance from the edge of the aperture towards a center of the aperture.

7. The system of claim 1, wherein the mirror structure is characterized such that a radiation wavelength of interest reflects from the mirror at highest reflectivity when a detected ray of radiation originates from a position of the sample.

8. The system of claim 7, wherein the mirror has a layer period that varies across a face of the mirror for reflecting the radiation wavelength of interest at highest reflectivity when the detected ray of radiation originates from the position of the sample.

9. The system of claim 1, wherein the mirror face is oriented at an angle of between about 10 and about 80 degrees from the axis of the beam from the source.

10. The system of claim 1, wherein the mirror face is oriented at an angle of about 45 degrees from the axis of the beam from the source.

11. The system of claim 1, wherein the mirror face is oriented at an angle of less than 45 degrees from the axis of the beam from the source.

12. The system of claim 1, wherein the face of the mirror is planar.

13. The system of claim 1, wherein the face of the mirror is concave.

14. The system of claim 1, wherein the face of the mirror is convex.

15. The system of claim 1, wherein the mirror includes an antireflective coating.

16. The system of claim 1, wherein the mirror comprises laminated layers of Si, Mo and $B_4C$.

17. The system of claim 1, wherein the mirror comprises laminated layers made from combinations of two or more of the following materials: Co, Ni, C, Ru, Y, Cr, $SiO_2$, $TiO_2$.

18. The system of claim 1, wherein the pixellated detector is a direct-illumination charge-coupled device.

19. The system of claim 1, further comprising a filter positioned between the mirror and the pixellated detector, the filter blocking a wavelength that is not of interest.

20. A system, comprising:
a multilayer mirror for reflecting at least a portion of radiation after a beam of the radiation encounters a sample, wherein the mirror has at least one of the following characteristics:
the mirror has an aperture therein for allowing radiation from the beam that is not scattered by the sample to pass therethrough; and/or
the mirror structure is characterized such that a radiation wavelength of interest reflects from the mirror at highest reflectivity when a detected ray of radiation originates from a position of the sample, wherein the mirror has a layer period that varies across a face of the mirror for reflecting the radiation wavelength of interest at highest reflectivity when the detected ray of radiation originates from the position of the sample.

21. A method, comprising:
directing a beam of radiation at a sample;
reflecting at least some of the radiation diffracted by the sample using a mirror, the mirror being oriented relative to the beam of radiation such that an axis of the beam of radiation intersects or passes through a face of the mirror;
not reflecting at least a majority of the radiation that is not diffracted by the sample; and
detecting at least some of the reflected radiation.

22. The method of claim 21, wherein a multilayer mirror reflects at least some of the radiation diffracted by the sample.

23. The method of claim 21, further comprising constructing a data set representative of the sample using the detected radiation.

24. The method of claim 21, further comprising repeating the method for multiple samples, and constructing a data set representative of the samples using the detected radiation, wherein the data set is three dimensional.

25. The method of claim 21, wherein the radiation includes X-rays.

26. The method of claim 21, wherein the radiation includes ultraviolet light.

27. A method, comprising:
directing a beam of radiation at a sample;
reflecting at least some of the radiation diffracted by the sample using a multilayer mirror; and
detecting at least some of the reflected radiations,
wherein the mirror has at least one of the following characteristics:
the mirror has an aperture therein for allowing radiation from the beam that is not scattered by the sample to pass therethrough; and/or
the mirror structure is characterized such that a radiation wavelength of interest reflects from the mirror at highest reflectivity when a detected ray of radiation originates from a position of the sample, wherein the mirror has a layer period that varies across a face of the mirror for reflecting the radiation wavelength of interest at highest reflectivity when the detected ray of radiation originates from the position of the sample.

* * * * *